US012698260B2

(12) United States Patent
Luthra et al.

(10) Patent No.: US 12,698,260 B2
(45) Date of Patent: Aug. 4, 2026

(54) SOLID STATE FORM OF CENTANAFADINE HCL AND PROCESS FOR PREPARATION THEREOF

(71) Applicant: ASSIA CHEMICAL INDUSTRIES LTD., Tel Aviv (IL)

(72) Inventors: Parven Kumar Luthra, Noida (IN); Anantha Rajmohan Muthusamy, Sivakasi (IN); Meenakshi Sundaram Somasundaram, Virudu Nagar DT (IN)

(73) Assignee: ASSIA CHEMICAL INDUSTRIES LTD., Tel Aviv (IL)

( * ) Notice: Subject to any disclaimer, the term of this patent is extended or adjusted under 35 U.S.C. 154(b) by 441 days.

(21) Appl. No.: 18/564,113

(22) PCT Filed: May 26, 2022

(86) PCT No.: PCT/US2022/030996
§ 371 (c)(1),
(2) Date: Nov. 27, 2023

(87) PCT Pub. No.: WO2022/256215
PCT Pub. Date: Dec. 8, 2022

(65) Prior Publication Data

US 2024/0246914 A1 Jul. 25, 2024

(30) Foreign Application Priority Data

May 31, 2021 (IN) ............................. 202111024127
Oct. 22, 2021 (IN) ............................. 202111048201

(51) Int. Cl.
*C07D 209/52* (2006.01)
*A61K 31/403* (2006.01)

(52) U.S. Cl.
CPC .......... *C07D 209/52* (2013.01); *A61K 31/403* (2013.01)

(58) Field of Classification Search
CPC ............................ C07D 209/52; A61K 31/403
USPC .......................................................... 514/412
See application file for complete search history.

(56) References Cited

U.S. PATENT DOCUMENTS 11,149,004 B2 10/2021 Chen et al.

FOREIGN PATENT DOCUMENTS

| | | | | | |
|---|---|---|---|---|---|
| WO | 2007016155 | A2 | | 2/2007 | |
| WO | WO2016205762 | A1 | * | 12/2016 | A61K 31/403 |
| WO | WO2018119291 | A1 | * | 6/2018 | A61K 31/403 |
| WO | WO2021075494 | A1 | * | 4/2021 | A61P 25/00 |

OTHER PUBLICATIONS

International Search Report and Written Opinion of the International Searching Authority issued in corresponding application PCT/US2022/030996 mailed Aug. 30, 2022 (13 pages).

* cited by examiner

*Primary Examiner* — Jeffrey S Lundgren
*Assistant Examiner* — Heather Dahlin
(74) *Attorney, Agent, or Firm* — Carter, DeLuca & Farrell, LLP

(57) ABSTRACT

The present disclosure encompasses a solid state form of Centanafadine HCl, processes for preparation thereof, and pharmaceutical compositions thereof.

12 Claims, 5 Drawing Sheets

X-ray powder diffraction pattern (XRPD) of Centanafadine HC1 Form CN1

X-ray powder diffraction pattern (XRPD) of Centanafadine HC1 purified Form CN1

Solid state $^{13}$C-NMR of Centanafadine HC1 Form CN1

11.149
23.364
24.480
26.492
29.419
30.533
31.847
47.864
53.078
125.515
126.771
128.479
131.762
132.645
134.478
227.767
228.943
230.762
233.970
234.931

SOLID STATE FORM OF CENTANAFADINE HCL AND PROCESS FOR PREPARATION THEREOF

CROSS REFERENCE TO RELATED APPLICATIONS

This application is a National Stage of, and claims priority to and the benefit of, International Patent Application No. PCT/US2022/030996, filed on May 26, 2022, which, in turn, claims the benefit of and priority to, Indian Provisional Application No. 202111024127, filed on May 31, 2021 and Indian Provisional Application No. 202111048201, filed on Oct. 22, 2021, the entire disclosures of each of which are incorporated by reference herein.

FIELD OF THE DISCLOSURE

The present disclosure encompasses a solid state form of Centanafadine HCl, processes for preparation thereof, and pharmaceutical compositions thereof.

BACKGROUND OF THE DISCLOSURE

Centanafadine, (1R,5S)-1-naphthalen-2-yl-3-azabicyclo [3.1.0]hexane, has the following chemical structure:

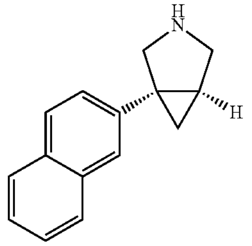 [SMILES: c1ccc2cc([C@]34CNC[C@H]3C4)ccc2c1]

Centanafadine is a serotonin-norepinephrine-dopamine reuptake inhibitor (SNDRI), and it is developed for the treatment of attention-deficit hyperactivity disorder (ADHD).

The compound is described in International Patent Appl. No. WO 2007/016155. Crystalline Forms of Centanafadine salts are described in International Patent Appl. No. WO 2016/205762.

Polymorphism, the occurrence of different crystalline forms, is a property of some molecules and molecular complexes. A single molecule may give rise to a variety of polymorphs having distinct crystal structures and physical properties like melting point, thermal behaviors (e.g., measured by thermogravimetric analysis ("TGA"), or differential scanning calorimetry ("DSC")), X-ray diffraction (XRD) pattern, infrared absorption fingerprint, and solid state ($^{13}C$) NMR spectrum. One or more of these techniques may be used to distinguish different polymorphic forms of a compound.

Different salts and solid state forms (including solvated forms) of an active pharmaceutical ingredient may possess different properties. Such variations in the properties of different salts and solid state forms and solvates may provide a basis for improving formulation, for example, by facilitating better processing or handling characteristics, changing the dissolution profile in a favorable direction, or improving stability (polymorph as well as chemical stability) and shelf-life. These variations in the properties of different salts and solid state forms may also offer improvements to the final dosage form, for instance, if they serve to improve bioavailability. Different salts and solid state forms and solvates of an active pharmaceutical ingredient may also give rise to a variety of polymorphs or crystalline forms, which may in turn provide additional opportunities to assess variations in the properties and characteristics of a solid active pharmaceutical ingredient.

Discovering new solid state forms and solvates of a pharmaceutical product may yield materials having desirable processing properties, such as ease of handling, ease of processing, storage stability, and ease of purification or as desirable intermediate crystal forms that facilitate conversion to other polymorphic forms. New solid state forms of a pharmaceutically useful compound can also provide an opportunity to improve the performance characteristics of a pharmaceutical product. It enlarges the repertoire of materials that a formulation scientist has available for formulation optimization, for example by providing a product with different properties, including a different crystal habit, higher crystallinity, or polymorphic stability, which may offer better processing or handling characteristics, improved dissolution profile, or improved shelf-life (chemical/physical stability). For at least these reasons, there is a need for additional solid state forms (including solvated forms) of Centanafadine.

SUMMARY OF THE DISCLOSURE

The present disclosure provides a crystalline polymorph of Centanafadine HCl, processes for preparation thereof, and pharmaceutical compositions thereof. This crystalline polymorph can be used to prepare other solid state forms of Centanafadine, Centanafadine salts and their solid state forms.

The present disclosure also provides uses of said solid state form of Centanafadine HCl in the preparation of other solid state forms of Centanafadine or salts thereof.

The present disclosure provides a crystalline polymorph of Centanafadine HCl for use in medicine, including for the treatment of attention-deficit hyperactivity disorder (ADHD).

The present disclosure also encompasses the use of the crystalline polymorph of Centanafadine HCl of the present disclosure for the preparation of pharmaceutical compositions and/or formulations.

In another aspect, the present disclosure provides pharmaceutical compositions comprising the crystalline polymorph of Centanafadine HCl according to the present disclosure.

The present disclosure includes processes for preparing the above mentioned pharmaceutical compositions. The processes include the crystalline polymorph of Centanafadine HCl with at least one pharmaceutically acceptable excipient.

The crystalline polymorph of Centanafadine HCl as defined herein and the pharmaceutical compositions or formulations of the crystalline polymorph of Centanafadine HCl may be used as medicaments, such as for the treatment of attention-deficit hyperactivity disorder (ADHD).

The present disclosure also provides methods of treating attention-deficit hyperactivity disorder (ADHD), by administering a therapeutically effective amount of the crystalline polymorph of Centanafadine HCl of the present disclosure, or at least one of the above pharmaceutical compositions, to a subject suffering from attention-deficit hyperactivity disorder (ADHD), or otherwise in need of the treatment.

The present disclosure also provides uses of the crystalline polymorph of Centanafadine HCl of the present disclosure, or at least one of the above pharmaceutical compositions, for the manufacture of medicaments for treating e.g. attention-deficit hyperactivity disorder (ADHD).

DETAILED DESCRIPTION OF THE DISCLOSURE

Figure 1:
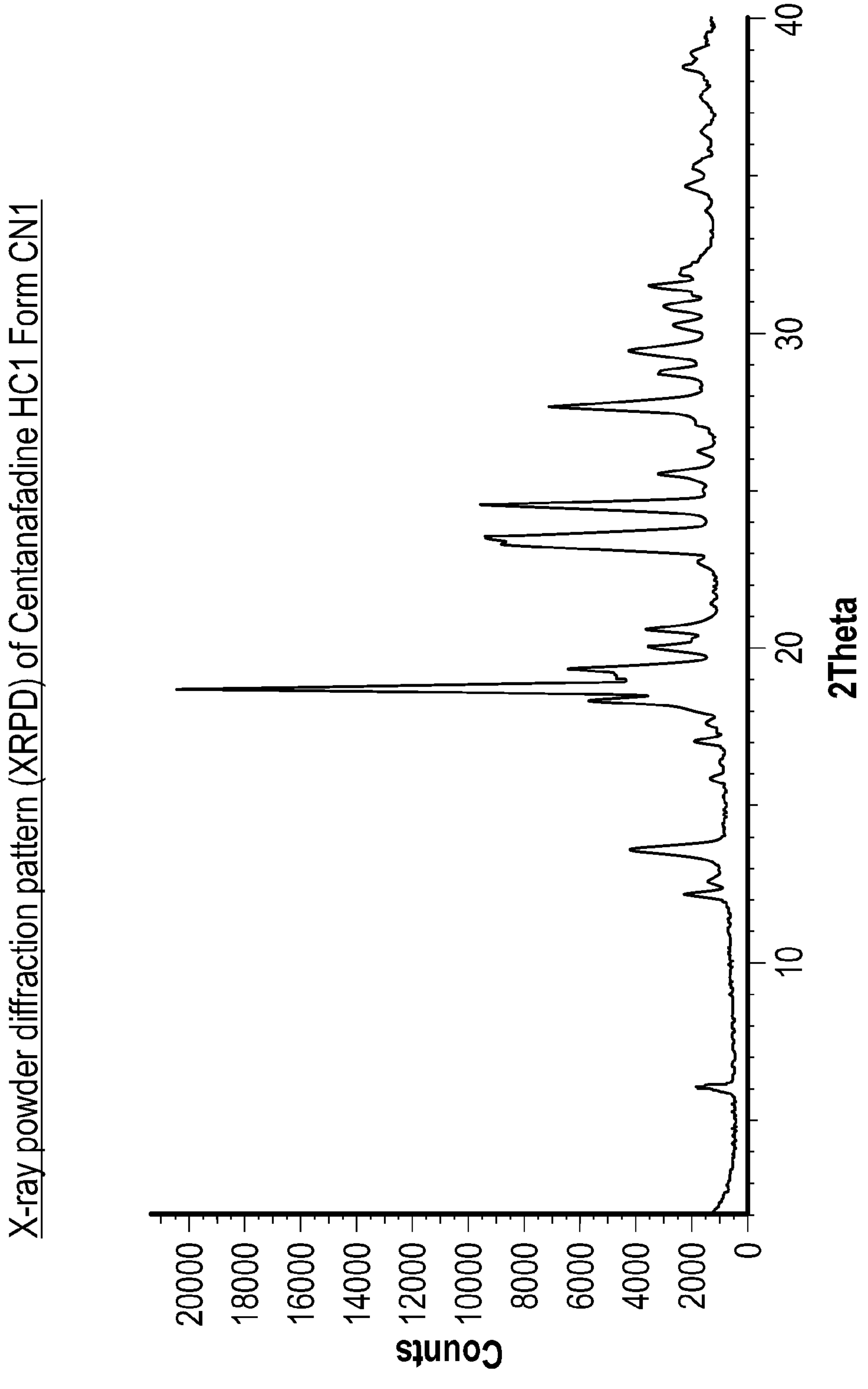
FIG. 1 shows a characteristic X-ray powder diffraction pattern (XRPD) of Centanafadine HCl Form CN1.

The present disclosure encompasses a crystalline polymorph of Centanafadine HCl, processes for preparation thereof, and pharmaceutical compositions thereof.

Solid state properties of Centanafadine HCl and crystalline polymorphs thereof can be influenced by controlling the conditions under which Centanafadine HCl and crystalline polymorphs thereof are obtained in solid form.

A solid state form (or polymorph) may be referred to herein as polymorphically pure or as substantially free of any other solid state (or polymorphic) forms. As used herein in this context, the expression "substantially free of any other forms" will be understood to mean that the solid state form contains about 20% (w/w) or less, about 10% (w/w) or less, about 5% (w/w) or less, about 2% (w/w) or less, about 1% (w/w) or less, or about 0% of any other forms of the subject compound as measured, for example, by XRPD. Thus, a crystalline polymorph of Centanafadine HCl described herein as substantially free of any other solid state forms would be understood to contain greater than about 80% (w/w), greater than about 90% (w/w), greater than about 95% (w/w), greater than about 98% (w/w), greater than about 99% (w/w), or about 100% of the subject crystalline polymorph of Centanafadine HCl. In some embodiments of the disclosure, the described crystalline polymorph of Centanafadine HCl may contain from about 1% to about 20% (w/w), from about 5% to about 20% (w/w), or from about 5% to about 10% (w/w) of one or more other crystalline polymorph of the same Centanafadine HCl.

Depending on which other crystalline polymorphs a comparison is made, the crystalline polymorph of Centanafadine HCl of the present disclosure may have advantageous properties selected from at least one of the following: chemical purity, flowability, solubility, dissolution rate, morphology or crystal habit, stability, such as chemical stability as well as thermal and mechanical stability with respect to polymorphic conversion, stability towards dehydration and/or storage stability, low content of residual solvent, a lower degree of hygroscopicity, flowability, and advantageous processing and handling characteristics such as compressibility and bulk density.

A solid state form, such as a crystal form or an amorphous form, may be referred to herein as being characterized by graphical data "as depicted in" or "as substantially depicted in" a Figure. Such data include, for example, powder X-ray diffractograms and solid state NMR spectra. As is well-known in the art, the graphical data potentially provides additional technical information to further define the respective solid state form (a so-called "fingerprint") which cannot necessarily be described by reference to numerical values or peak positions alone. In any event, the skilled person will understand that such graphical representations of data may be subject to small variations, e.g., in peak relative intensities and peak positions due to certain factors such as, but not limited to, variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms. A crystal form of Centanafadine HCl referred to herein as being characterized by graphical data "as depicted in" or "as substantially depicted in" a Figure will thus be understood to include any crystal forms of Centanafadine HCl characterized with the graphical data having such small variations, as are well known to the skilled person, in comparison with the Figure.

As used herein, and unless stated otherwise, the term "anhydrous" in relation to crystalline forms of Centanafadine HCl, relates to a crystalline form of Centanafadine HCl which does not include any crystalline water (or other solvents) in a defined, stoichiometric amount within the crystal. Moreover, an "anhydrous" form would generally not contain more than 1% (w/w), of either water or organic solvents as measured for example by TGA.

The term "solvate," as used herein and unless indicated otherwise, refers to a crystal form that incorporates a solvent in the crystal structure. When the solvent is water, the solvate is often referred to as a "hydrate." The solvent in a solvate may be present in either a stoichiometric or in a non-stoichiometric amount.

As used herein, the term "isolated" in reference to the crystalline polymorph of Centanafadine HCl of the present disclosure corresponds to a crystalline polymorph of Centanafadine HCl that is physically separated from the reaction mixture in which it is formed.

As used herein, unless stated otherwise, the XRPD measurements are taken using copper Kα radiation wavelength 1.5418 Å. XRPD peaks reported herein are measured using CuK α radiation, $\lambda$=1.5418 Å, typically at a temperature of 25±3° C.

A thing, e.g., a reaction mixture, may be characterized herein as being at, or allowed to come to "room temperature" or "ambient temperature," often abbreviated as "RT." This means that the temperature of the thing is close to, or the same as, that of the space, e.g., the room or fume hood, in which the thing is located. Typically, room temperature is from about 20° ° C. to about 30° C., or about 22° ° C. to about 27° C., or about 25° C.

The amount of solvent employed in a chemical process, e.g., a reaction or crystallization, may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending a 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding solvent X (1.5 v/v) to a 100 ml reaction mixture would indicate that 150 mL of solvent X was added.

A process or step may be referred to herein as being carried out "overnight." This refers to a time interval, e.g., for the process or step, that spans the time during the night, when that process or step may not be actively observed. This time interval is from about 8 to about 20 hours, or about 10-18 hours, in some cases about 16 hours.

As used herein, the term "reduced pressure" refers to a pressure that is less than atmospheric pressure. For example, reduced pressure is about 10 mbar to about 50 mbar.

As used herein and unless indicated otherwise, the term "ambient conditions" refer to atmospheric pressure and a temperature of 22-24° C.

The present disclosure includes a crystalline polymorph of Centanafadine HCl, designated Form CN1. The crystalline Form CN1 of Centanafadine HCl may be characterized by data selected from one or more of the following: an X-ray powder diffraction pattern substantially as depicted in FIG. 1 or in FIG. 2; an X-ray powder diffraction pattern having peaks at 12.6, 13.6, 18.7, 24.6 and 31.5 degrees 2-theta±0.2 degrees 2-theta; and combinations of these data.

Crystalline Form CN1 of Centanafadine HCl may be further characterized by an X-ray powder diffraction pattern having peaks at 12.6, 13.6, 18.7, 24.6 and 31.5 degrees 2-theta±0.2 degrees 2-theta, and also having any one, two, three, or four additional peaks selected from 23.4, 27.7, 29.4 and 30.9 degrees 2-theta±0.2 degrees 2-theta.

Figure 3A:
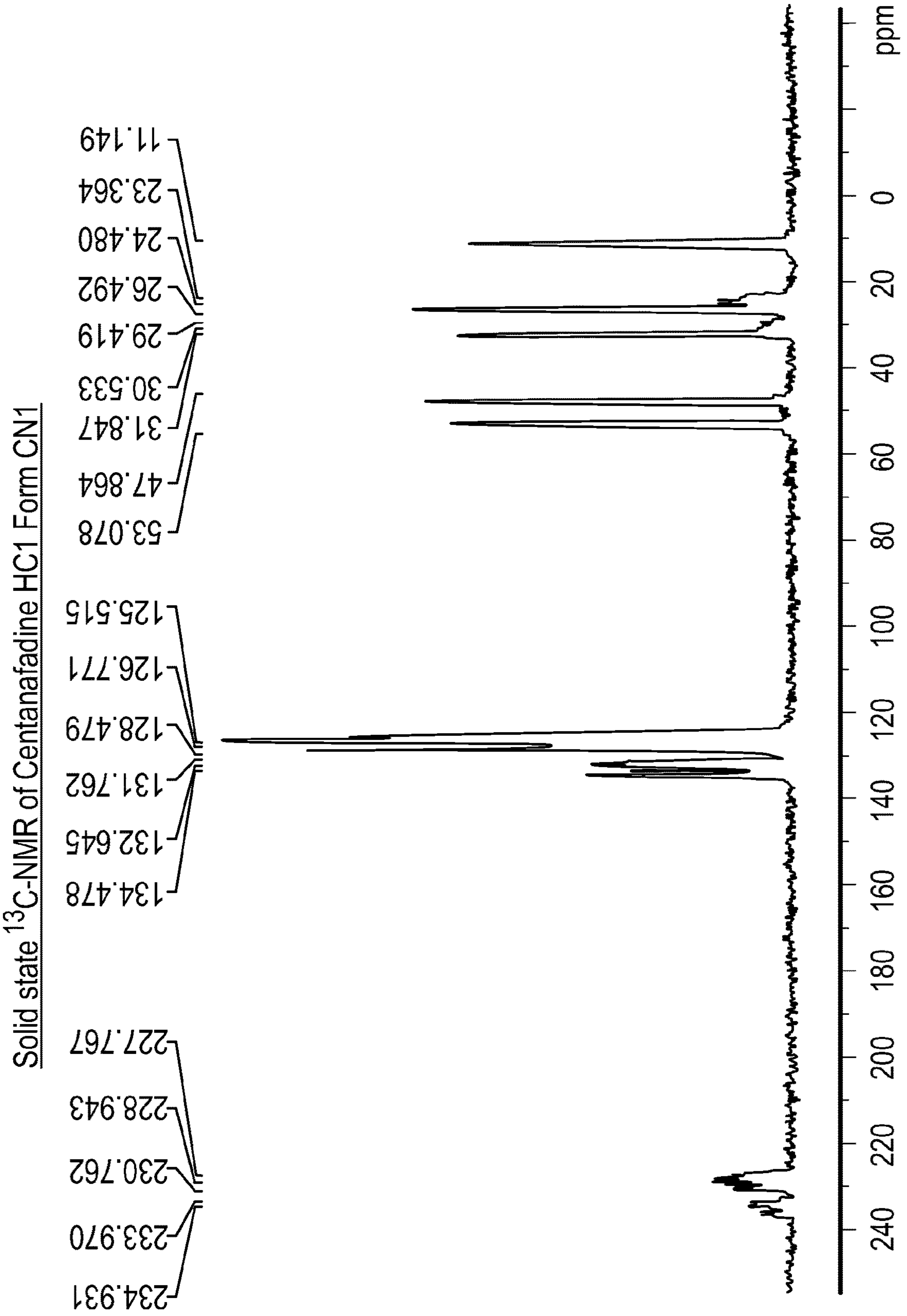
FIG. 3 shows a characteristic solid state $^{13}$C-NMR spectrum of purified Centanafadine HCl Form CN1 (FIG. 3*a*: full scan.
FIG. 3*b*: 0-100 ppm.
FIG. 3*c*: 100-200 ppm).
Figure 3B:
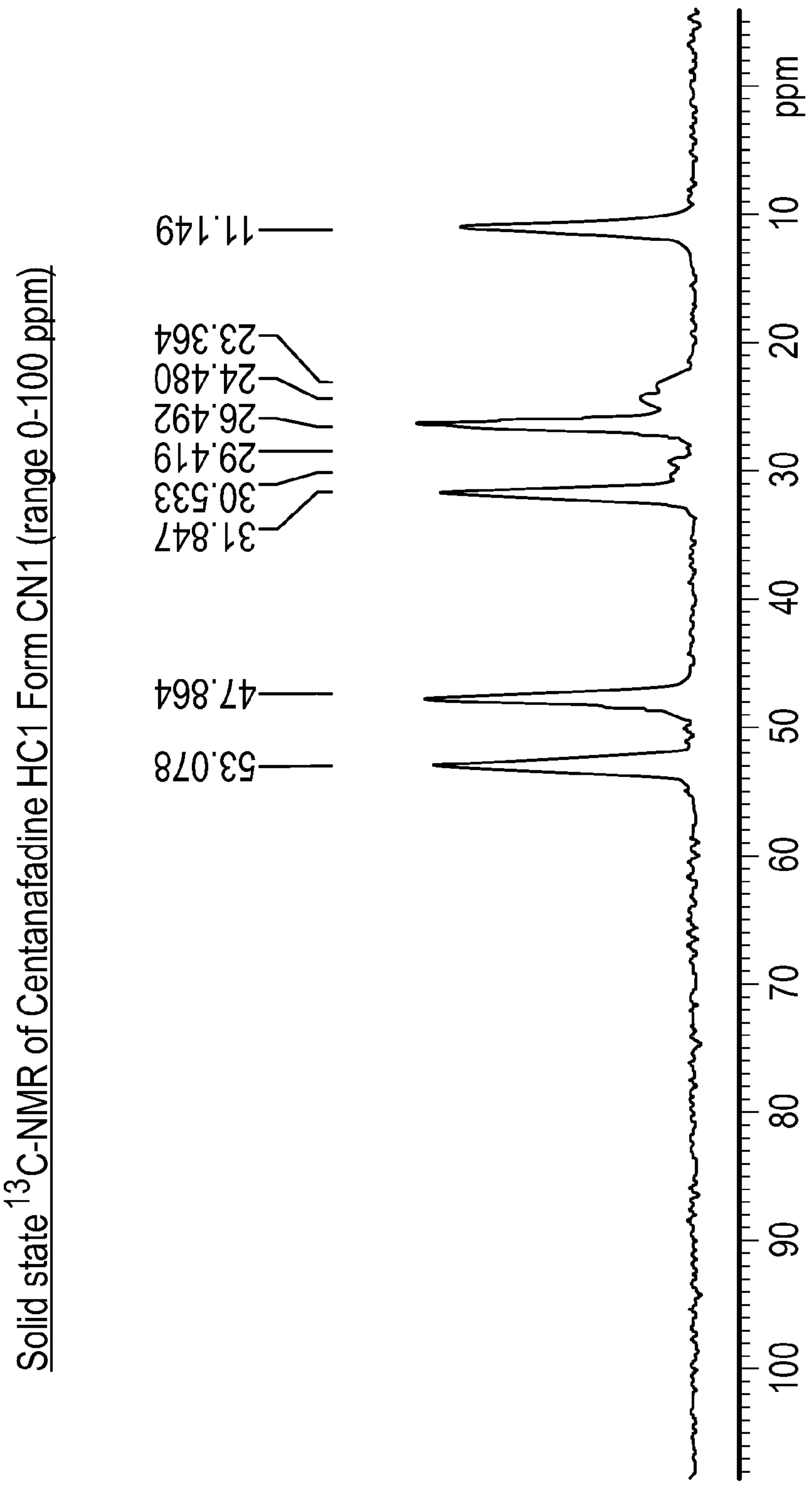
Figure 3C:
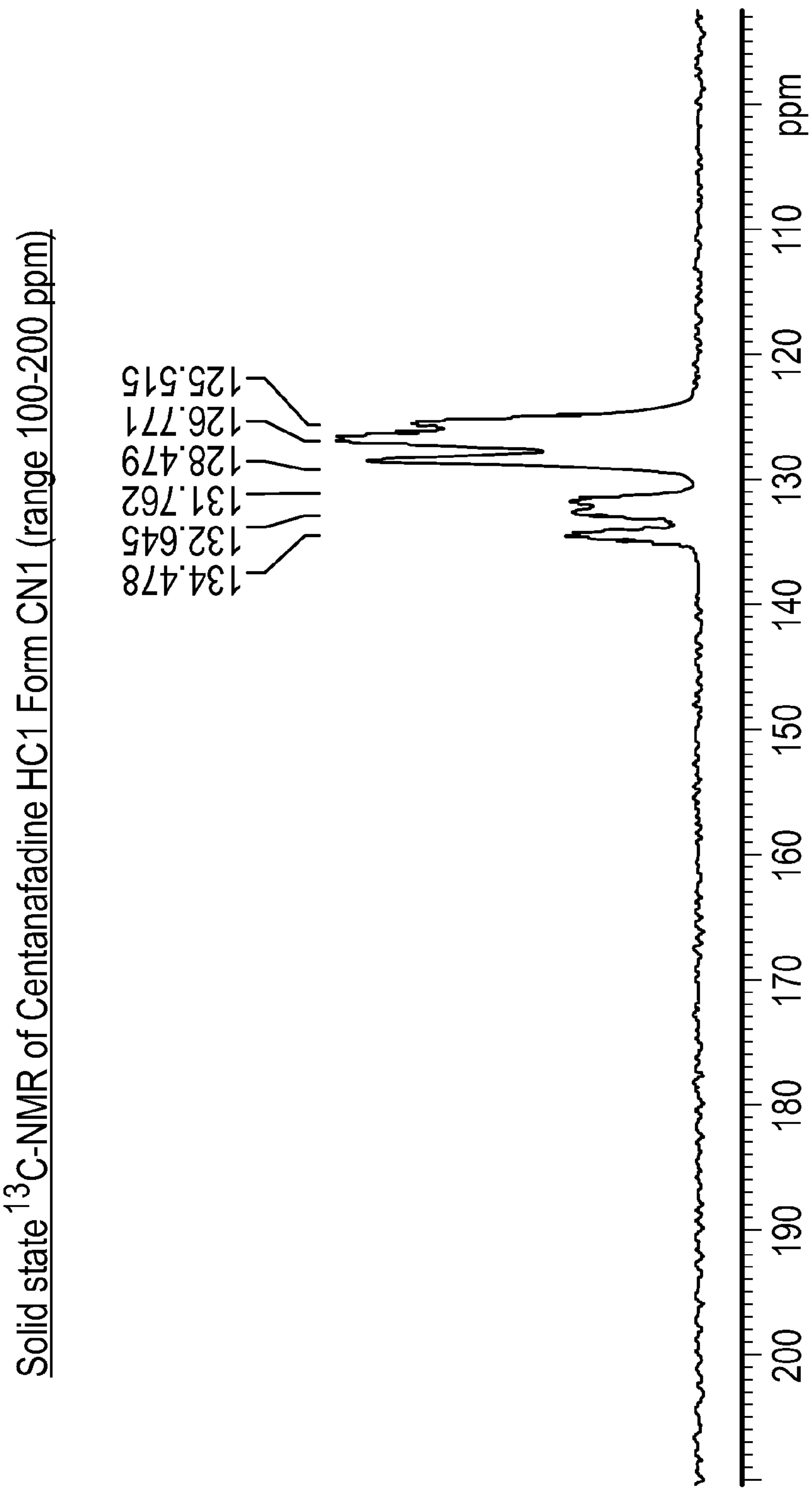

Crystalline Form CN1 of Centanafadine HCl may alternatively or additionally be characterized by data selected from one or more of the following: a solid state $^{13}C$ NMR spectrum with characteristic peaks at 11.1, 23.4, 29.4, 30.5, 128.5 and 131.8 ppm±0.2 ppm; a solid state $^{13}C$ NMR spectrum having the following chemical shift absolute differences from a peak at 47.9 ppm±2 ppm of 36.8, 24.5, 18.5, 17.4, 80.6 and 83.9 ppm±0.1 ppm; or by a solid state $^{13}C$ NMR having the following chemical shift difference from a peak at 11.1 ppm±1 ppm of −36.8 ppm±0.1 ppm; or by a solid state 13C-NMR spectrum substantially as depicted in FIGS. 3*a*, 3*b* and 3*c*; or combinations of these data.

In one embodiment of the present disclosure, crystalline Form CN1 of Centanafadine HCl is isolated.

Crystalline Form CN1 of Centanafadine HCl may be anhydrous.

Figure 2:
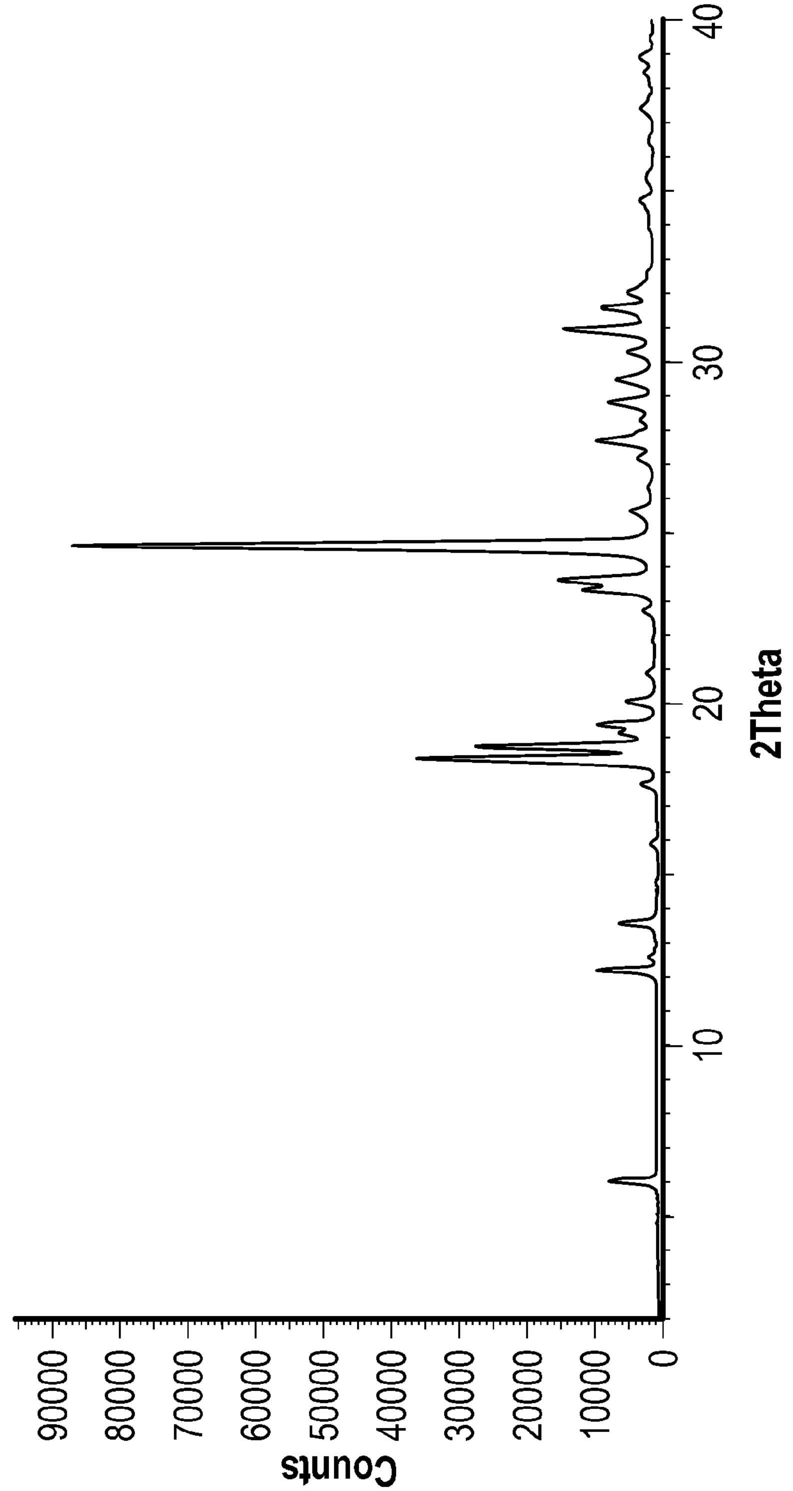
FIG. 2 shows a characteristic XRPD of a purified Centanafadine HCl Form CN1.

Crystalline Form CN1 of Centanafadine HCl may be characterized by each of the above characteristics alone/or by all possible combinations, e.g., an XRPD pattern having peaks at 12.6, 13.6, 18.7, 24.6 and 31.5 degrees 2-theta±0.2 degrees 2-theta; an XRPD pattern as depicted in FIG. 1 or in FIG. 2, and combinations thereof.

Crystalline Form CN1 of Centanafadine HCl is a stable crystalline Form upon storage and processing (e.g. grinding, pressure, heat, humidity).

Crystalline Form CN1 of Centanafadine HCl shows an improved solubility over a wide range of pH.

The above crystalline polymorph can be used to prepare other crystalline polymorphs of Centanafadine, Centanafadine salts and their solid state forms.

The present disclosure encompasses a process for preparing other solid state forms of Centanafadine, Centanafadine salts and solid state forms thereof. The process includes preparing Centanafadine HCl and solid state forms thereof by the processes of the present disclosure, and converting that salt to another Centanafadine salt. The conversion can be done, for example, by a process including basifying the above described solid state form of Centanafadine HCl, and reacting the obtained Centanafadine with an appropriate acid, to obtain the corresponding salt. Alternatively, the conversion can be done by salt switching, i.e., reacting a Centanafadine addition salt, with an acid having a pKa which is lower than the pKa of the acid of the first Centanafadine acid addition salt.

The present disclosure provides the above described crystalline polymorph of Centanafadine HCl for use in the preparation of pharmaceutical compositions comprising Centanafadine HCl and/or crystalline polymorphs thereof.

The present disclosure also encompasses the use of the crystalline polymorph of Centanafadine HCl of the present disclosure for the preparation of pharmaceutical compositions of the crystalline polymorph Centanafadine HCl.

The present disclosure includes processes for preparing the above mentioned pharmaceutical compositions. The processes include combining the crystalline polymorph of Centanafadine HCl of the present disclosure with at least one pharmaceutically acceptable excipient.

Pharmaceutical combinations or formulations of the present disclosure contain the solid state form of Centanafadine HCl of the present disclosure. In addition to the active ingredient, the pharmaceutical formulations of the present disclosure can contain one or more excipients. Excipients are added to the formulation for a variety of purposes.

Diluents increase the bulk of a solid pharmaceutical composition, and can make a pharmaceutical dosage form containing the composition easier for the patient and caregiver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol, and talc.

Solid pharmaceutical compositions that are compacted into a dosage form, such as a tablet, can include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate, and starch.

The dissolution rate of a compacted solid pharmaceutical composition in the patient's stomach can be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®), and starch.

Glidants can be added to improve the flowability of a non-compacted solid composition and to improve the accuracy of dosing. Excipients that can function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that can be included in the composition of the present disclosure include maltol, vanillin, ethyl vanillin, menthol, citric acid, fumaric acid, ethyl maltol, and tartaric acid.

Solid and liquid compositions can also be dyed using any pharmaceutically acceptable colorant to improve their appearance and/or facilitate patient identification of the product and unit dosage level.

In liquid pharmaceutical compositions of the present invention, Centanafadine HCl and any other solid excipients can be dissolved or suspended in a liquid carrier such as water, vegetable oil, alcohol, polyethylene glycol, propylene glycol, or glycerin.

Liquid pharmaceutical compositions can contain emulsifying agents to disperse uniformly throughout the composition an active ingredient or other excipient that is not soluble in the liquid carrier. Emulsifying agents that can be useful in liquid compositions of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions of the present invention can also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, xanthan gum and combinations thereof.

Sweetening agents such as sorbitol, saccharin, sodium saccharin, sucrose, aspartame, fructose, mannitol, and invert sugar can be added to improve the taste.

Preservatives and chelating agents such as alcohol, sodium benzoate, butylated hydroxyl toluene, butylated hydroxyanisole, and ethylenediamine tetraacetic acid can be added at levels safe for ingestion to improve storage stability.

According to the present disclosure, a liquid composition can also contain a buffer such as gluconic acid, lactic acid, citric acid, or acetic acid, sodium gluconate, sodium lactate, sodium citrate, or sodium acetate. Selection of excipients and the amounts used can be readily determined by the formulation scientist based upon experience and consideration of standard procedures and reference works in the field.

The solid compositions of the present disclosure include powders, granulates, aggregates, and compacted compositions. The dosages include dosages suitable for oral, buccal, rectal, parenteral (including subcutaneous, intramuscular, and intravenous), inhalant, and ophthalmic administration. Although the most suitable administration in any given case will depend on the nature and severity of the condition being treated, in embodiments the route of administration is oral. The dosages can be conveniently presented in unit dosage form and prepared by any of the methods well-known in the pharmaceutical arts.

Dosage forms include solid dosage forms like tablets, powders, capsules, suppositories, sachets, troches, and lozenges, as well as liquid syrups, suspensions, and elixirs.

The dosage form of the present disclosure can be a capsule containing the composition, such as a powdered or granulated solid composition of the disclosure, within either a hard or soft shell. The shell can be made from gelatin and optionally contain a plasticizer such as glycerin and/or sorbitol, an opacifying agent and/or colorant.

The active ingredient and excipients can be formulated into compositions and dosage forms according to methods known in the art.

A composition for tableting or capsule filling can be prepared by wet granulation. In wet granulation, some or all of the active ingredients and excipients in powder form are blended and then further mixed in the presence of a liquid, typically water, that causes the powders to clump into granules. The granulate is screened and/or milled, dried, and then screened and/or milled to the desired particle size. The granulate can then be tableted, or other excipients can be added prior to tableting, such as a glidant and/or a lubricant.

A tableting composition can be prepared conventionally by dry blending. For example, the blended composition of the actives and excipients can be compacted into a slug or a sheet and then comminuted into compacted granules. The compacted granules can subsequently be compressed into a tablet.

As an alternative to dry granulation, a blended composition can be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate, and colloidal silica. The proper use of these and other excipients in direct compression tableting is known to those in the art with experience and skill in particular formulation challenges of direct compression tableting.

A capsule filling of the present disclosure can include any of the aforementioned blends and granulates that were described with reference to tableting, but they are not subjected to a final tableting step.

A pharmaceutical formulation of Centanafadine HCl can be administered. Centanafadine HCl may be formulated for administration to a mammal, in embodiments to a human, by injection. Centanafadine HCl can be formulated, for example, as a viscous liquid solution or suspension, such as a clear solution, for injection. The formulation can contain one or more solvents. A suitable solvent can be selected by considering the solvent's physical and chemical stability at various pH levels, viscosity (which would allow for syringeability), fluidity, boiling point, miscibility, and purity. Suitable solvents include alcohol USP, benzyl alcohol NF, benzyl benzoate USP, and Castor oil USP. Additional substances can be added to the formulation such as buffers, solubilizers, and antioxidants, among others. Ansel et al., Pharmaceutical Dosage Forms and Drug Delivery Systems, 7th ed.

The crystalline polymorph of Centanafadine HCl and the pharmaceutical compositions and/or formulations of Centanafadine HCl of the present disclosure can be used as medicaments, in embodiments in the treatment of attention-deficit hyperactivity disorder (ADHD).

The present disclosure also provides methods of treating attention-deficit hyperactivity disorder (ADHD) by administering a therapeutically effective amount of any one or a combination of the crystalline polymorph of Centanafadine HCl of the present disclosure, or at least one of the above pharmaceutical compositions and/or formulations, to a subject in need of the treatment.

Having thus described the disclosure with reference to particular preferred embodiments and illustrative examples, those in the art can appreciate modifications to the disclosure as described and illustrated that do not depart from the spirit and scope of the disclosure as disclosed in the specification. The Examples are set forth to aid in understanding the disclosure but are not intended to, and should not be construed to limit its scope in any way.

Powder X-ray Diffraction ("XRPD") Method

X-Ray Diffraction was Performed on X-Ray Powder Diffractometer:

Bruker D8 Advance; CuKα radiation (λ=1.5418 Å); Lynx eye detector; laboratory temperature 22-25° C.; PMMA specimen holder ring with silicon low background. Prior to analysis, the samples were gently ground by means of mortar and pestle in order to obtain a fine powder. The ground sample was adjusted into a cavity of the sample holder and the surface of the sample was smoothed by means of a cover glass.

Measurement Parameters:

Scan range: 2-40 degrees 2-theta;
Scan mode: continuous;
Step size: 0.05 degrees;
Time per step: 0.5 s;
Sample spin: 30 rpm;
Sample holder: PMMA specimen holder ring with silicon low background.

All X-Ray Powder Diffraction peak values are calibrated with regard to standard silicon spiking in the sample.

Solid State $^{13}$C-NMR Method

Solid-state 13C-NMR spectra were measured at 11.7 T using a Bruker Avance III HD 500 US/WB NMR spectrometer (Karlsruhe, Germany, 2013) with 3.2 mm probe head. The $^{13}$C CP/MAS NMR spectra employing cross-polarization were acquired using the standard pulse scheme at spinning frequency of 15 kHz and a room temperature (300 K). The recycle delay was 8 s and the cross-polarization contact time was 2 ms. The $^{13}$C scale was referenced to α-glycine (176.03 ppm for $^{13}$C). Frictional heating of the spinning samples was offset by active cooling, and the temperature calibration was performed with $Pb(NO_3)_2$. The NMR spectrometer was completely calibrated and all experimental parameters were carefully optimized prior the investigation. Magic angle was set using KBr during standard optimization procedure and homogeneity of magnetic field was optimized using adamantane sample (resulting line-width at half-height Δυ½ was less than 3.5 Hz at 250 ms of acquisition time).

EXAMPLES

Preparation of Starting Materials

Centanafadine HCl can be prepared according to methods known from the literature, for example as described in International Publication No. WO 2007/016155.

Example 1: Preparation of Centanafadine HCl Form CN1

Centanafadine HCl (0.05 grams) was taken in a 50 mL RB flask and was dissolved in 4.5 mL of 1-propanol at 70° C. Added 12 mL of precooled Acetonitrile at 5° C. to the hot solution and cooled to 0° C. in 1 hour. The resulting clear solution was subjected to evaporation under reduced pressure about 50 mbar at 70° C. for about 20 minutes. The obtained solid analyzed by XRD and designated as Centanafadine HCl Form CN1.

Centanafadine HCl Form CN1 is anhydrous crystalline form.

Example 2: Preparation of Centanafadine HCl Form CN1

Centanafadine HCl (0.05 grams) was taken in a 50 mL RB flask and was dissolved in 4.5 mL of 1-propanol at 70° C. Added 12 mL of precooled n-butyl acetate at 5° C. to the hot solution and cooled to 0° C. in 1 hour. The resulting clear solution was subjected to evaporation under reduced pressure about 50 mbar at 70° C. for about 20 minutes. The obtained solid analyzed by XRD and designated as Centanafadine HCl Form CN1.

Centanafadine HCl Form CN1 is anhydrous crystalline form.

Example 3: Preparation of Centanafadine HCl Form CN1

Centanafadine HCl (5.0 grams) was taken in a 100 mL RB flask and was dissolved in 50 mL of Methanol at 70° C. and filtered. In a second flask 100 mg of Form CN1 seeds (about 1.0-2.5% w/w) were added to 500 mL of precooled n-propyl acetate at 0-5° C. The filtered Methanol solution was added to the n-propyl acetate solution in 10 minutes at 0-5° C. A precipitate was obtained, stirred for 2 hours at 0-5° C., filtered and dried under suction for 1 hour at 25° C. The solid was further dried under vacuum at 60° C. for 2 hours. The solid was analyzed by XRD and designated as Centanafadine HCl Purified Form CN1.

Example 4: Preparation of Centanafadine HCl Form CN1

Centanafadine HCl (1.0 gram) was taken in a 50 mL RB flask and was dissolved in 10 mL of Methanol at 70° C. and filtered. In a second flask 25 mg of Form CN1 seeds (about 1.0-2.5% w/w) were added to 100 mL of precooled Methyl tert-butyl ether at 0-5° C. The filtered Methanol solution was added to the Methyl tert-butyl ether solution in 10 minutes at 0-5° C. A precipitate was obtained and stirred for 2 hours at 0-5° C., filtered and dried under suction for 1 hour at 25° C. The solid was further dried under vacuum at 60° C. for 2 hours. The obtained solid was analyzed by XRD and designated as Centanafadine HCl Purified Form CN1.

The invention claimed is:

1. A crystalline form CN1 of Centanafadine HCl, which is characterized by data selected from one or more of the following:

i) an XRPD pattern having peaks at 12.6, 13.6, 18.7, 24.6 and 31.5 degrees 2-theta±0.2 degrees 2-theta;
ii) an XRPD pattern as depicted in FIG. 1;
iii) an XRPD pattern as depicted in FIG. 2;
iv) a solid state $^{13}$C-NMR spectrum with peaks at 11.1, 23.4, 29.4, 30.5, 128.5 and 131.8 ppm±0.2 ppm;
v) a solid state $^{13}$C-NMR spectrum having the following chemical shift absolute differences from a peak at 47.9 ppm±2 ppm of 36.8, 24.5, 18.5, 17.4, 80.6 and 83.9 ppm±0.1 ppm; or vi) a solid state $^{13}C$-NMR spectrum substantially as depicted in FIG. 3*a*.

2. The crystalline form of Centanafadine HCl according to claim 1, which is characterized by an XRPD pattern having peaks at 12.6, 13.6, 18.7, 24.6 and 31.5 degrees 2-theta±0.2 degrees 2-theta, and also having one, two, three or four additional peaks selected from 23.4, 27.7, 29.4 and 30.9 degrees 2-theta±0.2 degrees 2-theta.

3. A pharmaceutical composition comprising the crystalline form according to claim 1.

4. A pharmaceutical formulation comprising the crystalline form according to claim 1, and at least one pharmaceutically acceptable excipient.

5. A medicament comprising the crystalline form according to claim 1.

6. A method of treating attention-deficit hyperactivity disorder (ADHD), comprising administering a therapeutically effective amount of the crystalline form according to claim 1 to a subject suffering from said disorder.

7. A pharmaceutical composition comprising a crystalline form according to claim 2.

8. A pharmaceutical formulation comprising a crystalline form according to claim 2 and at least one pharmaceutically acceptable excipient.

9. A medicament comprising the crystalline form according to claim 2.

10. A method of treating attention-deficit hyperactivity disorder (ADHD), comprising administering a therapeutically effective amount of the crystalline form according to claim 2 to a subject suffering from said disorder.

11. A method of treating attention-deficit hyperactivity disorder (ADHD), comprising administering a therapeutically effective amount of the pharmaceutical composition of claim 3 to a subject suffering from said disorder.

12. A method of treating attention-deficit hyperactivity disorder (ADHD), comprising administering a therapeutically effective amount of the pharmaceutical formulation according to claim 4 to a subject suffering from said disorder.

* * * * *